United States Patent
Rai et al.

(10) Patent No.: US 11,747,275 B2
(45) Date of Patent: Sep. 5, 2023

(54) SYSTEM AND METHOD FOR NON-INVASIVE REAL-TIME PREDICTION OF LIQUID FOOD QUALITY WITHIN ENCLOSED PACKAGE

(71) Applicant: Tata Consultancy Services Limited, Mumbai (IN)

(72) Inventors: Beena Rai, Pune (IN); Jayita Dutta, Pune (IN); Parijat Deshpande, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 29 days.

(21) Appl. No.: 17/562,133

(22) Filed: Dec. 27, 2021

(65) Prior Publication Data
US 2022/0205905 A1 Jun. 30, 2022

(30) Foreign Application Priority Data
Dec. 28, 2020 (IN) .............................. 202021056751

(51) Int. Cl.
*G01N 21/359* (2014.01)
*G01N 33/04* (2006.01)

(52) U.S. Cl.
CPC ........... *G01N 21/359* (2013.01); *G01N 33/04* (2013.01)

(58) Field of Classification Search
CPC ............... G01N 21/359; G01N 33/04; G01N 2201/129; G01N 21/3577; G01N 33/14
See application file for complete search history.

(56) References Cited

U.S. PATENT DOCUMENTS

| | | | | |
|---|---|---|---|---|
| 9,453,826 | B2 * | 9/2016 | Muldoon | G01N 21/65 |
| 2009/0321646 | A1 * | 12/2009 | Cozzolino | G01N 21/31 |
| | | | | 250/339.05 |
| 2020/0225149 | A1 * | 7/2020 | Shi | G01N 21/359 |

FOREIGN PATENT DOCUMENTS

CN 108732111 A * 11/2018 ............. A47B 73/00

OTHER PUBLICATIONS

Harris et al., Non-Invasive Digital Technologies to Assess Wine Quality Traits and Provenance through the Bottle, Dec. 23, 2022, Fermentation, vol. 9, 10, pp. 1-13 (Year: 2022).*

(Continued)

*Primary Examiner* — Christine S. Kim
(74) *Attorney, Agent, or Firm* — Finnegan, Henderson, Farabow, Garrett & Dunner LLP

(57) ABSTRACT

State of the art food quality measurement techniques fail to determine quality of the food item once it is packed and sealed in an enclosed package. The disclosure herein generally relates to food quality prediction, and, more particularly, to a system and method for predicting liquid food quality in a non-invasive manner. A near infra-red (NIR) radiation is transmitted through a semi-transparent opening configured on an enclosed package containing a liquid food item and the resulting NIR reflection spectra is collected. The quality of the liquid food item is estimated by correlating a plurality of features derived from the NIR reflection spectra with the concentration of the biomarker contained in the liquid food item, using a trained machine learning model and the remaining shelf life of the liquid food item is estimated based on the concentration of the biomarker.

12 Claims, 7 Drawing Sheets

(56) References Cited

OTHER PUBLICATIONS

Muniz et al., Milk quality control requirement evaluation using a handheld near infrared reflectance spectrophotometer and a bespoke mobile application, Dec. 10, 2019, Journal of Food Composition and Analysis, vol. 86, pp. 1-8. (Year: 2019).*

Alfouzan et al., Near Infra Red (NIR)-Based Classification of Orange Juice, 2017, 2017 International Conference on Electrical and Computing Technologies and Applications (ICECTA), pp. 1-5 (Year: 2017).*

Shen et al., Detection of Adulteration in Freshly Squeezed Orange Juice by Electronic Nose and Infrared Spectroscopy, 2016, Czech J. Food Sci., vol. 34, pp. 224-232 (Year: 2016).*

Riu et al., Rapid Analysis of Milk Using Low-Cost Pocket-Size NIR Spectrometers and Multivariate Analysis, Aug. 10, 2020, Foods vol. 9, pp. 1-18. (Year: 2020).*

Lu et al., Milk Spoilage: Methods and Practices of Detecting Milk Quality, Jul. 2013, Food and Nutrition Sciences, vol. 4, pp. 113-123. (Year: 2013).*

Al-Qadiri et al., Monitoring Quality Loss of Pasteurized Skim Milk Using Visible and Short Wavelength Near-Infrared Spectroscopy and Multivariate Analysis, Apr. 2008, J. Dairy Sci. vol. 91, pp. 950-958. (Year: 2008).*

Assaad, "Non-destructive, non-invasive, in-line real-time phase-based reflectance for quality monitoring of fruit," International Journal on Smart Sensing and Intelligent Systems, 13:1 (2020).

Beghi et al., "Electronic nose and visible-near infrared spectroscopy in fruit and vegetable monitoring," Reviews in Analytical Chemistry (2017).

Bwambok et al., "QCM Sensor Arrays, Electroanalytical Techniques and NIR Spectroscopy Coupled to Multivariate Analysis for Quality Assessment of Food Products, Raw Materials, Ingredients and Foodborne Pathogen Detection: Challenges and Breakthroughs," Sensors, 20 (2020).

Dixit et al., "Developments and Challenges in Online NIR Spectroscopy for Meat Processing," Comprehensive Reviews in Food Science and Food Safety, 16 (2017).

* cited by examiner

SYSTEM AND METHOD FOR NON-INVASIVE REAL-TIME PREDICTION OF LIQUID FOOD QUALITY WITHIN ENCLOSED PACKAGE

PRIORITY CLAIM

This U.S. patent application claims priority under 35 U.S.C. § 119 to: India Application No. 202021056751, filed on Dec. 28, 2020. The entire contents of the aforementioned application are incorporated herein by reference.

TECHNICAL FIELD

This disclosure relates generally to food quality prediction, and more particularly to a system and method for non-invasive real-time prediction of liquid food quality within enclosed package.

BACKGROUND

In order to enhance shelf-life, liquid food-items are packaged within air-tight containers. Such containers may include various layers to prevent the exposure of the liquid food item with outside environment, thus imparting a comparatively longer shelf-life to the packaged liquid food than those liquid food items that are kept with improper packaging or no packaging. However, even with use of such packaging, there are scenarios that leads to huge wastage of packaged food items.

The liquid food-items within the air-tight containers cannot be evaluated for their quality post packaging i.e., once the air-tight containers are sealed, the information about the quality of the contents within the air-tight containers is not available and one has to rely solely on the printed date on the packaging of the air-tight containers. Further, at times this can prove to be misleading and contents of the airtight containers may be good post expiry or worse and inedible even prior to expiry. Such situations can arise due to temperature shocks received by the air-tight containers during its shelf and transportation lifetime.

Main reason behind the food wastage is inability to monitor the variation of food quality in real-time under different supply chain scenarios. To address this challenge real time monitoring and prediction of food quality for variety of foods becomes essential. This would enable dynamic decisions on rerouting, repurposing, and recycling.

SUMMARY

Embodiments of the present disclosure present technological improvements as solutions to one or more of the above-mentioned technical problems recognized by the inventors in conventional systems. For example, in one embodiment, a method for non-invasive real-time prediction of liquid food quality within enclosed package is provided. The method includes transmitting, via one or more hardware processors, a near infra-red radiation (NIR) signal over a range of frequencies using a near infra-red radiation (NIR) device through a semi-transparent window configured on an enclosed package containing a liquid food item; obtaining, via the one or more hardware processors, the resulting near infra-red radiation (NIR) reflection spectra inside the enclosed package containing the liquid food item using an electronic device; deriving, using a trained machine learning model via the one or more hardware processors, a plurality of features from the near infra-red radiation (NIR) reflection spectra obtained, wherein the trained machine learning model is trained on a near infra-red radiation (NIR) spectra obtained over a range of frequencies to characterize the liquid food item and correlate with quality; performing, via the one or more hardware processors, a correlation of the plurality of derived features with the concentration of a biomarker contained in the liquid food item, and estimating a remaining shelf-life of the liquid food item based on the concentration of the biomarker; and estimating, via the one or more hardware processors, the quality of the liquid food item based on the correlation and the estimated remaining shelf-life.

In another aspect, there is provided a system for non-invasive real-time prediction of liquid food quality within enclosed package. The system comprises: a memory storing instructions; one or more communication interfaces; and one or more hardware processors coupled to the memory via the one or more communication interfaces, wherein the one or more hardware processors are configured by the instructions to: transmit, a near infra-red radiation (NIR) signal over a range of frequencies using a near infra-red radiation (NIR) device through a semi-transparent window configured on an enclosed package containing a liquid food item. The system further comprises obtaining, the resulting near infra-red radiation (NIR) reflection spectra inside the enclosed package containing the liquid food item using an electronic device; derive, using a trained machine learning model, a plurality of features from the near infra-red radiation (NIR) reflection spectra obtained, wherein the trained machine learning model is trained on a near infra-red radiation (NIR) spectra obtained over a range of frequencies to characterize the liquid food item and correlate with quality; perform, a correlation of the plurality of derived features with the concentration of a biomarker contained in the liquid food item, and estimating a remaining shelf-life of the liquid food item based on the concentration of the biomarker; and estimate, the quality of the liquid food item based on the correlation and the estimated remaining shelf-life.

In yet another aspect, there are provided one or more non-transitory machine-readable information storage mediums comprising one or more instructions which when executed by one or more hardware processors cause transmitting, via one or more hardware processors, a near infra-red radiation (NIR) signal over a range of frequencies using a near infra-red radiation (NIR) device through a semi-transparent window configured on an enclosed package containing a liquid food item; obtaining, via the one or more hardware processors, the resulting near infra-red radiation (NIR) reflection spectra inside the enclosed package containing the liquid food item using an electronic device; deriving, using a trained machine learning model via the one or more hardware processors, a plurality of features from the near infra-red radiation (NIR) reflection spectra obtained, wherein the trained machine learning model is trained on a near infra-red radiation (NIR) spectra obtained over a range of frequencies to characterize the liquid food item and correlate with quality; performing, via the one or more hardware processors, a correlation of the plurality of derived features with the concentration of a biomarker contained in the liquid food item, and estimating a remaining shelf-life of the liquid food item based on the concentration of the biomarker; and estimating, via the one or more hardware processors, the quality of the liquid food item based on the correlation and the estimated remaining shelf-life.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
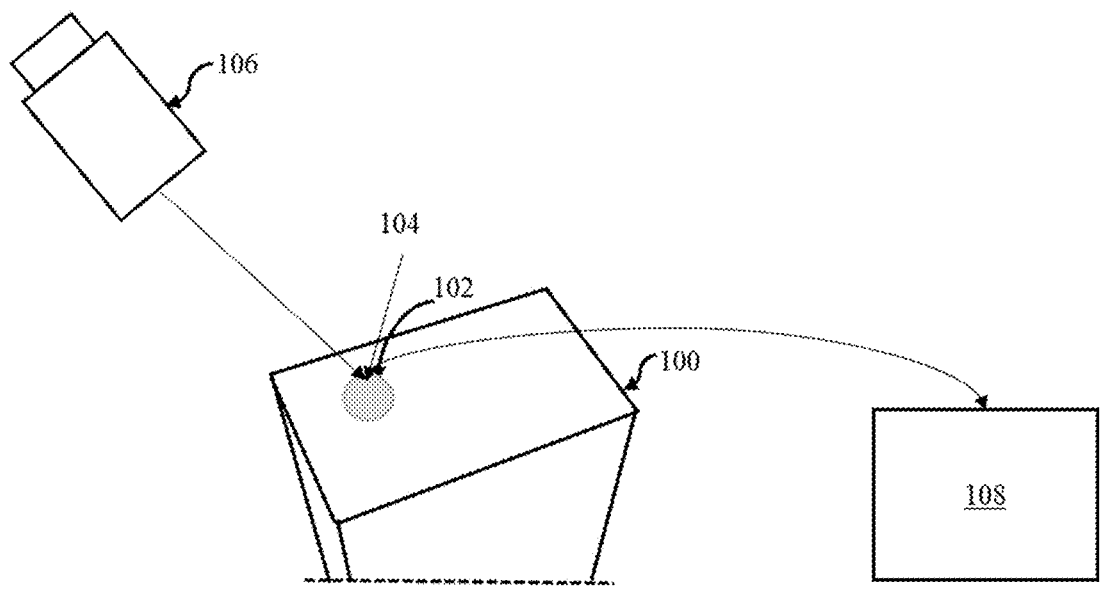
FIG. 1 illustrates an example of an enclosed package for liquid food items in accordance with an example embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Food wastage due to lack of any effective real-time food monitoring method has led to a huge economic loss. This situation can be avoided if there is a provision for monitoring the food quality in real-time which can appraise the consumers regarding the food quality inside the package in real-time and noninvasively. Accordingly, even if the expiry date for food item is reached, and the food inside package is still consumable and in good quality, then the stake holders such as retailers, distributors and so on can opt for dynamic pricing to sell the packaged food. Customer can also rely on the quality of the food item and buy it even after the indicated expiry dates on the food package.

In one of the known techniques, near infra-red radiation (NIR) spectroscopy was used to determine the concentration of various compositions in milk. However, such solution does not assess the quality and remaining shelf life of liquids within packaged or air-tight containers. Hence, it is challenging to implement this conventional method for assessing the quality of the liquid food within packaged or air-tight containers. Further, in another known technique, the quality of food is predicted or estimated by finding the correlation between the food signature and the food quality. Here the word "signature" refers to a vector representation of food under different supply chain scenarios, as the food degrades over a period due to the variation in chemical composition, images, texture, firmness and gases emitted.

Various embodiments disclosed herein provide method and apparatus for quality monitoring of packaged liquid food item in a non-invasive manner. For example, in an embodiment, the disclosed apparatus includes a semi-transparent window configured on a portion of the enclosed package for transmitting the near infra-red radiation (NIR) signal through the contents of the enclosed package. A NIR reflection spectra which is obtained by virtue of the enclosed package dimensions and the contents of the enclosed package are measured. The NIR reflection spectra is then correlated with food quality using a machine learning based model.

Referring now to the drawings, and more particularly to FIG. 1 through FIG. 4D, where similar reference characters denote corresponding features consistently throughout the figures, there are shown preferred embodiments and these embodiments are described in the context of the following exemplary system and/or method.

FIG. 1 illustrates an example of an enclosed package for liquid food items in accordance with an example embodiment of the present disclosure. For the brevity of description, the enclosed package 100 is shown to assume a cuboid shape, however it will be understood that the enclosed package 100 may assume any shape other than the shape and size shown.

In an embodiment, a semi-transparent window 102 may be configured towards the inner walls of the enclosed package as depicted in FIG. 1. Herein, it will be understood that for the brevity of description and ease of understanding, the semitransparent window 102 is shown to assume form of a circular shaped window. However, in alternate implementations, the semi-transparent window 102 may assume any shape other than the shape shown here.

In an embodiment, the semi-transparent window 102 can be configured by altering a transparent opening 104 of the existing enclosed package (for example, the enclosed package 100) material for employing the NIR based sensor or NIR/hyperspectral device 106 to transmit and measure the reflected spectra and thereby to predict the quality of the food item, more specifically liquid food item inside the enclosed package 100. The transparent opening 104 is configured on the enclosed package (for example, enclosed package 100) towards the inner walls of the enclosed package as depicted in FIG. 1. Herein, it will be understood that for the brevity of description and ease of understanding, the transparent opening 104 is shown to assume form of a circular shaped window. However, in alternate implementations, the transparent opening 104 may assume any shape other than the shape shown here.

In an embodiment, the near infra-red radiation (NIR) signal is transmitted through the semi-transparent window 102 configured on the enclosed package 100 using a NIR/hyperspectral device (NIR based sensor) 106. The NIR signal wavelength can be swept over a range of 700-2500 nm based on the particular liquid food item inside the enclosed package 100. The NIR/hyperspectral device 106 is a portable, external gadget which is used for multiple enclosed packages for a wide variety of contents, for example, juice milk, soup, and so on. The NIR/hyperspectral device 106 detects the wavelengths of light adjacent to a visible light spectrum. Further, in the present disclosure, the NIR device 106 acts as a transducer i.e., the NIR device 106 transmits the NIR signal through the enclosed package 100 and also receive the NIR reflection spectra from the enclosed package 100. The NIR reflection spectra is obtained when a NIR signal is transmitted though the semitransparent window 102 configured on the enclosed package 100. The data related to the NIR reflection spectra which is received by the NIR device 106 is collected by an electronic device 108 for prediction of quality of liquid food item contained inside the enclosed package (for example, the enclosed package 100). The electronic device 108 can be a laptop, desktop or mobile. In the present disclosure, the electronic device 108 is configured to include machine learning (NL) based models or algorithms. The collected NIR reflection spectra data include information about the contents of the enclosed package (for example, the enclosed package 100) for example, milk, juice, soups, etc. Further, the information related to the collected NIR reflection spectra serve as a transfer function of the package dimensions, package contents and the quality of the contents of the enclosed package (for example, enclosed package 100). In real-time, the NIR reflection spectra data will be collected by the NIR device 106 and sent to an android/iOS application. The machine learning (ML) based application runs in the background of the android/iOS application that predicts the quality of liquid food item within packaged enclosed package (for example, the enclosed package 100) in real time.

In an embodiment, the collected NIR reflection spectra data are then correlated with the liquid food quality item within enclosed package (for example, the enclosed package 100) using the machine learning based models comprised in the electronic device 108. In the present disclosure, the NIR reflection spectra changes over time for the NIR input or signal which is swept across various wavelengths range of 780 to 2,500 nm. Further, as the food degrades there is a corresponding change in an interference pattern of the reflected lights within the enclosed package. This interference pattern can thus be correlated to the quality of the food. The response i.e., received NIR reflection spectra including the specific features such as information related to the contents of the enclosed package (for example, the enclosed package 100) is trained via machine learning (ML) based models to provide a correlation between food quality, more specifically quality of liquid food item inside the enclosed package (for example, the enclosed package 100). Further, the machine learning (ML) models/algorithms comprised in the electronic device 108 are based on the reflectance of light. In the present disclosure, the machine learning model helps in ascertaining the quality of the contents for example, juice having excess acidity for safe consumption or milk curdled without a user having to open the enclosed package (for example, enclosed package 100). More specifically, the machine learning models are based on the correlation between the food quality with the received signal related to NIR reflection spectra over a range of frequencies. Training the machine learning model is further explained in the later sections.

In an embodiment, the present disclosure provides a lumped model which accounts for prediction of degradation of the overall quality of liquids or liquid foods enclosed within enclosed package (for example, the enclosed package 100) and considers reflections within the enclosed package (for example, the enclosed package 100) for the prediction of quality. In an example embodiment of the present disclosure, the lumped model for orange juice is developed based on the NIR reflection spectra of the orange juice and the ascorbic acid (AA) concentration in the orange juice. It is to be noted the ascorbic acid is the biomarker for the orange juice and the biomarker is specific to the liquid food item. The NIR reflection spectra is fed into the lumped model which is able to provide insights regarding the quality of the orange juice in real time by determining the AA concentration from the NIR reflection spectra. Further, the information about the quality of the orange juice and the remaining shelf life of the orange juice is derived from the AA concentration. In an embodiment of the present disclosure the word "NIR signature" represents the changes in the NIR reflection spectra due to the change of chemical composition, etc., over time, i.e., due to the degradation of liquids or liquid foods or liquid food items over time. Further, the 'NIR signature' of the NIR reflection spectra generated when the liquid food item is good will be different from the NIR reflection spectra data, which is generated when the liquid food item is turns bad or spoiled. Hence, the quality of the liquid food item is determined based on "good" food spectra and "spoiled" food spectra.

In an embodiment, the NIR reflection spectra obtained due to the changes in the physio-chemical properties of liquid food item over a period of time may be captured by an electronic device 108 that may be capable of predicting the quality of the liquid food item and a remaining shelf-life of the liquid food item. A system (embodied in the electronic device 108) for predicting the quality of liquid food item contained in the enclosed package, and a method therefore are explained further with reference to FIGS. 2 and 3, respectively.

Figure 2:
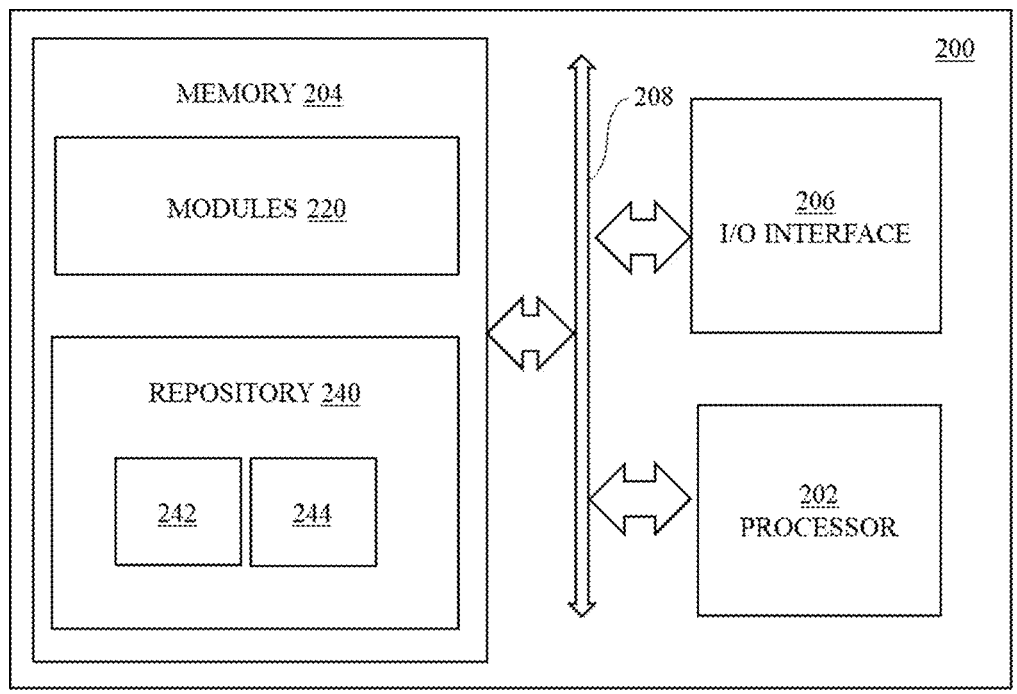
FIG. 2 illustrates a block diagram of a system for predicting quality of a liquid food item contained in the enclosed package (of FIG. 1) is illustrated, according to some embodiments of the present disclosure.

Referring now to FIG. 2, a block diagram of a system 200 for predicting quality of a liquid food item contained in a enclosed package (for example, the enclosed package 100 of FIG. 1) is illustrated, according to some embodiments of the present disclosure. The system 200 is capable of training a model for predicting the quality of liquid food item based on the NIR reflection spectra obtained inside the enclosed package as depicted in FIG. 1.

The system 200 includes or is otherwise in communication with one or more hardware processors such as a processor 202, at least one memory such as a memory 204, and an I/O interface 206. The processor 202, memory 204, and the I/O interface 206 may be coupled by a system bus such as a system bus 208 or a similar mechanism. The I/O interface 206 may include a variety of software and hardware interfaces, for example, a web interface, a graphical user interface, and the like. The interfaces 206 may include a variety of software and hardware interfaces, for example, interfaces for peripheral device(s), such as a keyboard, a mouse, an external memory, a camera device, and a printer. Further, the interfaces 206 may enable the system 200 to communicate with other devices, such as web servers and external databases. The interfaces 206 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 206 may include one or more ports for connecting a number of computing systems with one another or to another server computer. The I/O interface 206 may include one or more ports for connecting a number of devices to one another or to another server.

The hardware processor 202 may be implemented as one or more microprocessors, microcomputers, microcontrollers, digital signal processors, central processing units, state machines, logic circuitries, and/or any devices that manipulate signals based on operational instructions. Among other capabilities, the hardware processor 202 is configured to fetch and execute computer-readable instructions stored in the memory 204.

The memory 204 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. In an embodiment, the memory 204 includes a plurality of modules 220 and a repository 240 for storing data processed, received, and generated by one or more of the modules 220. The modules 220 may include routines, programs, objects, components, data structures, and so on, which perform particular tasks or implement particular abstract data types.

The repository 240, amongst other things, includes a system database 242 and other data 244. The other data 244 may include data generated as a result of the execution of one or more modules in the other modules 220. In an embodiment, the repository 240 may store the data of the NIR reflection spectra associated with the prediction of food quality. For example, the data may include a data associated with the NIR reflection spectra obtained from inside the enclosed package 100. In an embodiment, the repository 240 may store the data associated with the concentration of the biomarkers specific to the liquid food item contained in the enclosed package 100 and their progression which is required to estimate the remaining shelf for each liquid food item for example, juice, milk etc. A method of quality prediction of a liquid food item contained in the enclosed package (for example, the enclosed package 100) by using the system (for example, the system 200) is described further with reference to FIG. 3.

Figure 3:
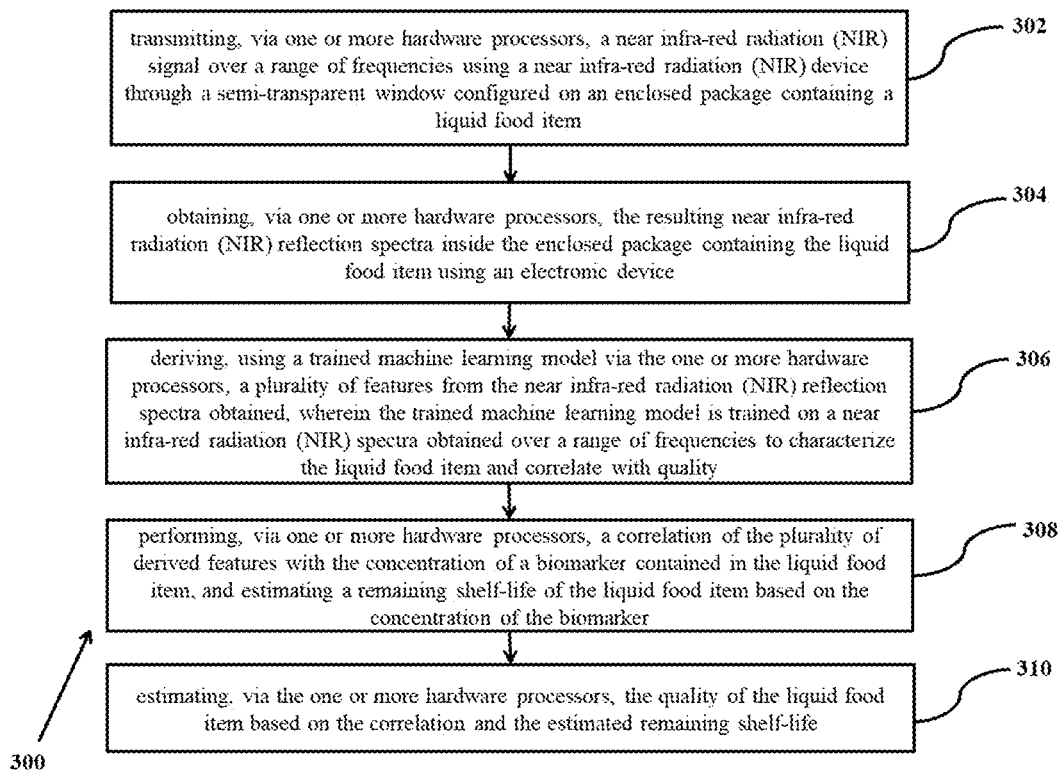
FIG. 3 illustrates a method for predicting quality of a liquid food item contained in the enclosed package (of FIG. 1) in accordance with some embodiments of the present disclosure.

Referring to FIG. 3, a flow diagram of a method 300 for predicting quality of a liquid food item contained in the enclosed package (for example, the enclosed package 100) is described in accordance with an example embodiment. The method 300 depicted in the flow chart may be executed by a system, for example, the system, 200 of FIG. 2. In an example embodiment, the system 200 may be embodied in a computing device, as will be described further in the description.

Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 300 are described with help of system 200. However, the operations of the method 300 can be described and/or practiced by using any other system.

At step 302, the one or more hardware processors transmit a near infra-red radiation (NIR) signal over a range of frequencies using a near infra-red radiation (NIR) device through a semi-transparent window configured on an enclosed package (for example, the enclosed package 100) containing a liquid food item. At step 304, the one or more hardware processors obtain the resulting near infra-red radiation (NIR) reflection spectra inside the enclosed package (for example, the enclosed package 100) containing the liquid food item using an electronic device. At step 306, the one or more hardware processors, derive, using a trained machine learning model, a plurality of features from the near infra-red radiation (NIR) reflection spectra obtained, wherein the trained machine learning model is trained on a near infra-red radiation (NIR) spectra obtained over a range of frequencies to characterize the liquid food item and correlate with quality. In an embodiment of the present disclosure, the plurality of features can include area under the curve of the NIR reflection spectra, localized changes in the slope across the curve, height of the peaks, mean, variance, spread of the curve, wavelengths at which the peaks appear. At step 308, the one or more hardware processors, perform a correlation of the plurality of derived features with the concentration of a biomarker contained in the liquid food item and estimate a remaining shelf-life of the liquid food item based on the concentration of the biomarker. At step 310, the one or more hardware processors, estimates the quality of the liquid food item based on the correlation and the estimated remaining shelf-life.

In an embodiment of the present disclosure, the machine learning model is trained using a training dataset which comprises of a plurality of training features derived from the near infra-red radiation (NIR) reflection spectra obtained over the range of frequencies and a plurality of concentration of training biomarkers. Further, a correlation of the plurality of training features derived from the near infra-red radiation (NIR) reflection spectra with the plurality of concentration of the training biomarkers is performed and the remaining shelf-life of the plurality of liquid food items is estimated based on the plurality of concentration of the training biomarkers. Further, the machine learning model is trained to estimate the quality of the liquid food item based on the obtained correlation and the estimated remaining shelf-life. As mentioned above, the spoilage of the liquid food item contained in the enclosed package is correlated to the biomarker threshold for considering the degradation in quality and labeling the data in terms of quality/freshness index with respect to the biomarker threshold. At, lab experiments are performed to monitor the NIR signature at different concentrations of biomarkers specific to the plurality of liquid food items. The NIR signature observed when the biomarker concentration reaches its threshold, wherein the liquid food item is labelled bad. The machine learning model is trained on these time-series data namely, concentration of the biomarker, corresponding NIR signature change for prediction of quality in terms of the remaining shelf life.

FIG. 4A through 4D shows a use case example illustrating the detection of spoilage in an orange Juice based on NIR reflection spectra and the concentration of ascorbic acid in accordance with some embodiments of the present disclosure. The spoilage of orange juice occurs through both enzymatic and non-enzymatic pathways. In case of aseptically packaged orange juices, the enzymatic pathways are inhibited in order to prolong shelf life. Hence only the non-enzymatic browning occurs in such juices, during transportation & storage. The concentrations of compounds such as ascorbic acid, sugars (fructose, glucose, sucrose), dissolved & headspace oxygen, 5-hydroxymethyl furfural and furfural in orange juice changes (increases/decreases) over time. Orange juice is a rich source of Vitamin C (ascorbic acid), having ~425 mg/L at the time of packaging. The ascorbic acid degradation/spoilage is one of the principal ways by which the quality of the orange juice is commonly judged. As understood from the previous sections, the spoilage is correlated to the ascorbic acid (AA) threshold for considering the degradation in quality and labeling the data in terms of quality/freshness index with respect to the AA threshold of 200 mg/L. At, lab experiments are performed to monitor the NIR signature at different concentrations of AA in orange juice. The NIR signature observed when AA concentration. reaches 200 mg/L, the orange juice is labelled bad. A model is trained on these time-series data namely, conc of AA, corresponding signature change for prediction of quality in terms of the remaining shelf life.

Figure 4A:
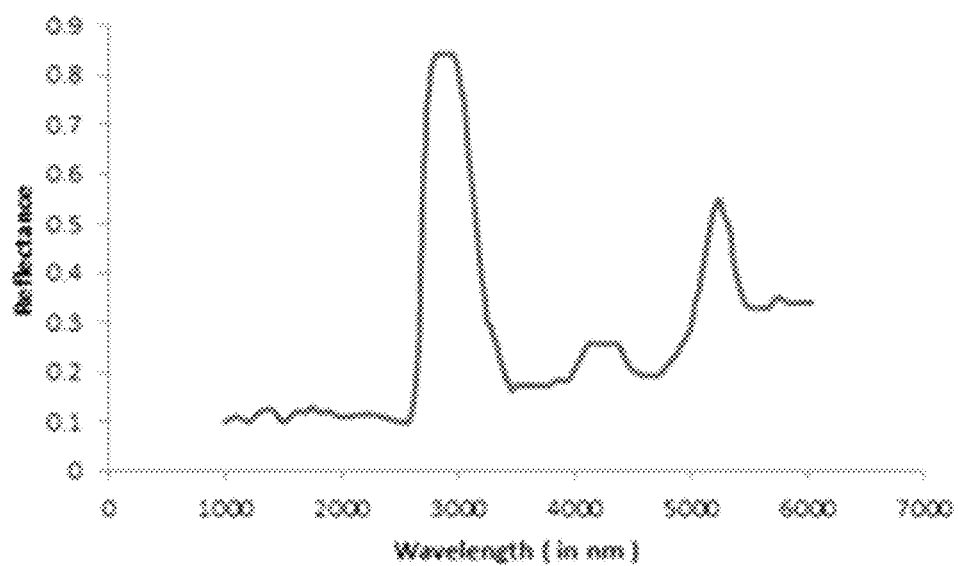
FIG. 4A through 4D shows a use case example illustrating the detection of spoilage in an orange Juice based on NIR reflection spectra and concentration of Ascorbic Acid (AA) in accordance with some embodiments of the present disclosure.
Figure 4B:
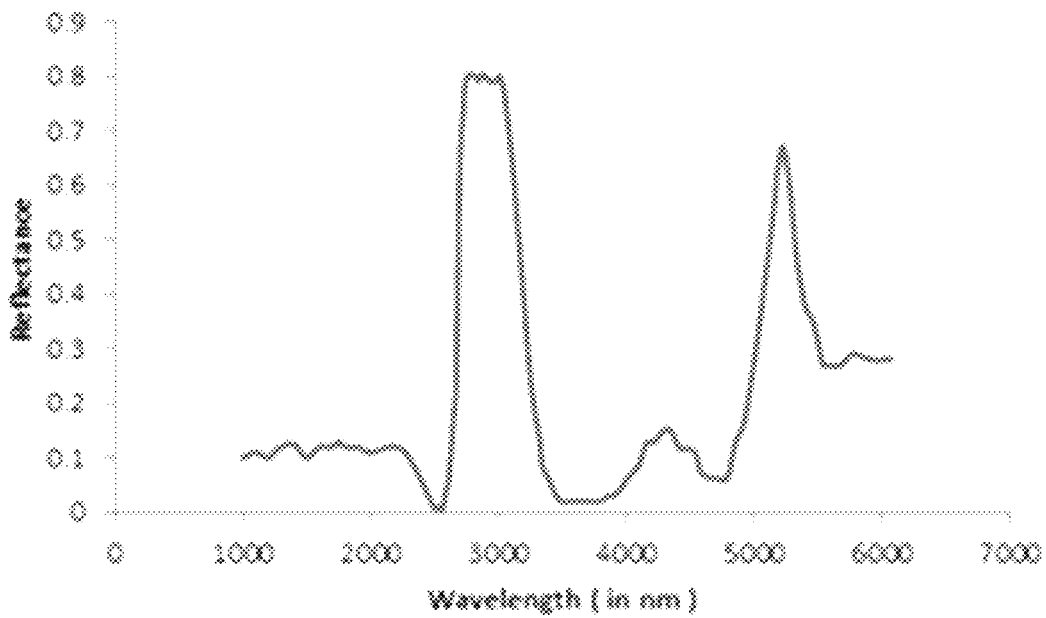
Figure 4C:
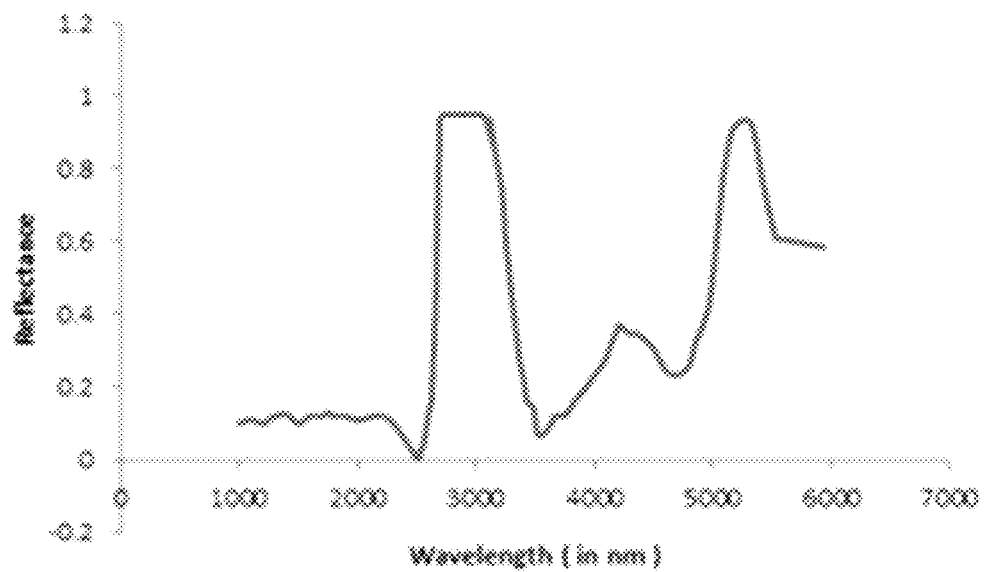
Figure 4D:
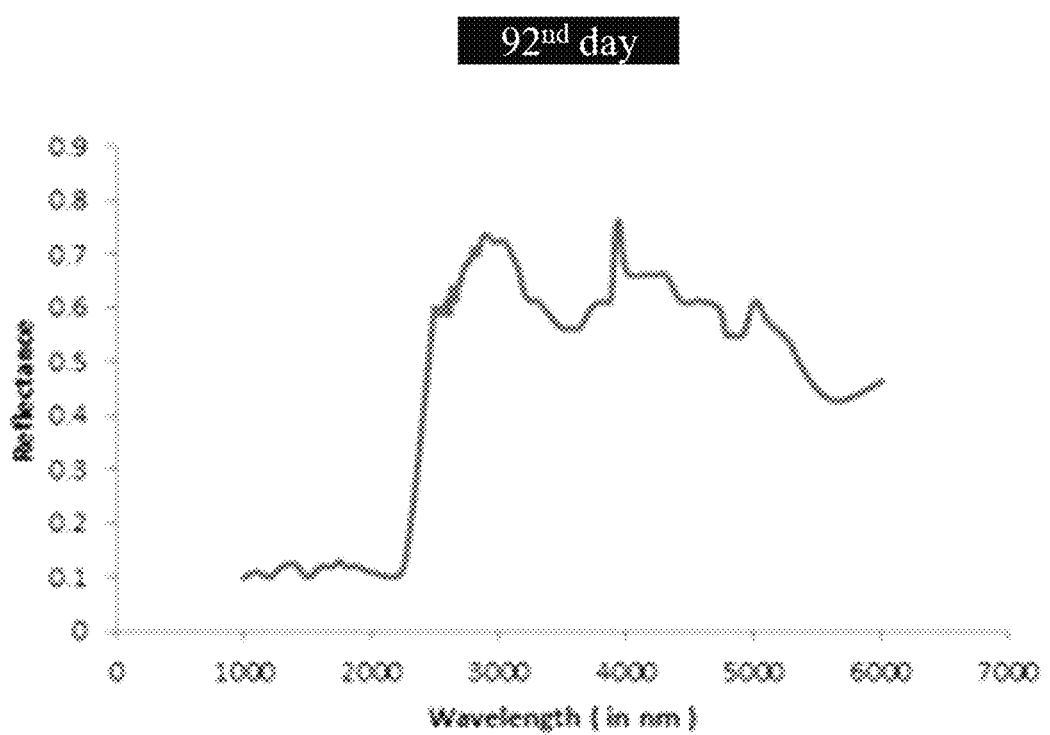

In an example embodiment, variation of NIR reflection spectra of orange juice with respect to the variation in the concentration of Ascorbic Acid (biomarker) over time is depicted in FIG. 4A through 4D. FIG. 4A depicts the variation of NIR reflection spectra of orange juice at $0^{th}$ day when the concentration of the ascorbic acid in the orange juice is 425 mg/L and wherein the remaining shelf life=92 days. FIG. 4B depicts the variation of NIR reflection spectra of orange juice at $14^{th}$ day when the concentration of the ascorbic acid in the orange juice is 365 mg/L and wherein the remaining shelf life=78 days. FIG. 4C depicts the variation of NIR reflection spectra of orange juice at $31^{st}$ day when the concentration of the ascorbic acid in the orange juice is 340 mg/L and wherein the remaining shelf life=61 days. FIG. 4D depicts the variation of NIR reflection spectra of orange juice at $92^{nd}$ day when the concentration of the ascorbic acid in the orange juice is 200 mg/L and wherein the remaining shelf life=0 days. It can be observed from the FIGS. 4A through 4D, there is a significant change in the area under the curve, height of peaks and spread of the curve of the NIR reflection spectra with the variation in the concentration of the ascorbic acid over time. Further, it is to be noted that, when the concentration of the Ascorbic Acid present in the orange juice reaches its threshold, for example in case of Ascorbic acid, the threshold is 200 mg/L, the orange juice is considered non-ideal for consumption or in other words, the orange juice is considered to be spoiled. It is to be understood by a person having ordinary skill in the art or a person skilled in the art that the above uses case or example shall not be construed as limiting the scope of the present disclosure. Further it is to be noted that the biomarker is specific to the liquid food item contained in the enclosed package.

In real-time this trained machine learning model acts as a soft sensor. The NIR reflection spectra is observed through the transparent window 104 on the enclosed package (for example, Tetrapak). In an example implementation, a dedicated mobile application is developed which allows user to scan the NIR reflection spectra. The trained machine learning model/soft sensor in the background which is linked to this application (locally or over cloud) considers the NIR reflection spectra as input to the trained machine learning model, estimates the corresponding ascorbic acid concentration at that time and correlates the NIR reflection spectra with the estimated ascorbic acid concentration. The trained machine learning model finally estimates the remaining shelf life based on the correlation and the remaining shelf life and the same is shown to the user in the mobile application.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Various embodiments disclosed herein provide method and system for estimating quality of food item packaged in an enclosed package. The embodiment of present disclosure herein addresses unresolved problem of monitoring and estimation of food quality no-invasively based on the NIR reflection spectra obtained inside the enclosed package. The NIR reflection spectra is obtained by transmitting a NIR radiation through the semi-transparent window configured on the enclosed package. The real-time quality monitoring may allow concerned stake holders to take dynamic decisions on repricing, reusing, recycling and repurposing, and so on and thus reduce food wastage and economic loss.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g., any kind of computer like a server or a personal computer, or the like, or any combination thereof. The device may also include means which could be e.g., hardware means like e.g., an application-specific integrated circuit (ASIC), a field-programmable gate array (FPGA), or a combination of hardware and software means, e.g., an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g., using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor-implemented method, comprising:
   transmitting, via one or more hardware processors, a near infra-red radiation (NIR) signal over a range of frequencies using a near infra-red radiation (NIR) device through a semi-transparent window configured on an enclosed package containing a liquid food item, wherein the semi-transparent window is configured on a portion of the enclosed package for transmitting the near infra-red radiation (NIR) signal on to the liquid food item;
   scanning, by a user via a mobile application, a near infra-red radiation (NIR reflection spectra resulting from reflection of the near infra-red radiation (NIR) signal over the liquid food item;
   transmitting by the user via the mobile application, a data related to the near infra-red radiation (NIR) reflection to an electronic device having a machine learning model;
   deriving, using the machine learning model via the one or more hardware processors, a plurality of features from the near infra-red radiation (NIR) reflection spectra obtained, wherein the machine learning model runs in a background of the mobile application and the machine learning mode is trained on a near infra-red radiation (NIR) spectra obtained over a range of frequencies to characterize the liquid food item and correlate with quality, wherein the plurality of features comprises an area under a curve of the NIR reflection spectra, localized changes in a slope across the curve, height of peaks of the curve, mean, variance, spread of the curve, wavelengths of the peaks, and wherein the machine learning model is trained on time-series data of a concentration of a biomarker contained in the liquid food item and a near infra-red radiation (NIR) signature for prediction of quality in terms of a remaining shelf life;
   performing, via the one or more hardware processors, a correlation of the plurality of derived features with the concentration of the biomarker contained in the liquid food item, and estimating the remaining shelf-life of the liquid food item based on the concentration of the biomarker, wherein NIR signature of the concentration of the biomarkers contained in the liquid food item is monitored, wherein the NIR signature represents changes in the NIR reflection spectra due to change of chemical composition over time due to degradation of the liquid food items, and wherein a spoilage of the liquid food item contained in the enclosed package is detected by correlating the NIR signature to a biomarker threshold for considering degradation in quality, and to label the liquid food item in terms of a quality index with respect to the biomarker threshold;
   estimating, via the one or more hardware processors, the quality of the liquid food item based on the correlation and the estimated remaining shelf-life; and
   displaying to the user on the mobile application, the quality of the liquid food item based on the correlation and the estimated remaining shelf-life.

2. The processor implemented method of claim 1, wherein the semi-transparent window configured on the enclosed package is used for near infra-red radiation (NIR) imaging.

3. The processor implemented method of claim 1, wherein step of training the machine learning model further comprises:
   (i) obtaining a training dataset comprising of a plurality of training features derived from the near infra-red radiation (NIR) reflection spectra obtained over the range of frequencies and a plurality of concentration of training biomarkers, wherein the near infra-red radiation (NIR) reflection spectra and the concentration of the training biomarkers are associated with a plurality of liquid food items;
   (ii) performing a correlation of the plurality of training features derived from the near infra-red radiation (NIR) reflection spectra with the plurality of concentration of the training biomarkers comprised in the obtained training dataset;
   (iii) estimating the remaining shelf-life of the plurality of liquid food items based on the plurality of concentration of the training biomarkers; and
   (iv) training the machine learning model to estimate the quality of the liquid food item based on the obtained correlation and the estimated remaining shelf-life.

4. The processor implemented method of claim 1, wherein the biomarker used in the estimation of the quality of the liquid food item is specific to the liquid food item contained inside the enclosed package.

5. A system, comprising:
   a memory storing instructions;
   one or more communication interfaces; and
   one or more hardware processors coupled to the memory via the one or more communication interfaces, wherein the one or more hardware processors are configured by the instructions to:
   transmit, a near infra-red radiation (NIR) signal over a range of frequencies using a near infra-red radiation (NIR) device through a semi-transparent window configured on an enclosed package containing a liquid food item, wherein the semi-transparent window is configured on a portion of the enclosed package for transmitting the near infra-red radiation (NIR) signal on to the liquid food item;
   scan, by a user via a mobile application, a near infra-red radiation (NIR) reflection spectra resulting from reflection of the near infra-red radiation (NIR) signal over the liquid food item;
   transmit, by the user via the mobile application, a data related to the near infra-red radiation (NIR) reflection to an electronic device having a machine learning model;

derive, using the machine learning model, a plurality of features from the near infra-red radiation (NIR) reflection spectra obtained, wherein the machine learning model runs in a background of the mobile application and the machine learning mode is trained on a near infra-red radiation (NIR) spectra obtained over a range of frequencies to characterize the liquid food item and correlate with quality, wherein the plurality of features comprises an area under a curve of the NIR reflection spectra, localized changes in a slope across the curve, height of peaks of the curve, mean, variance, spread of the curve, wavelengths of the peaks, and wherein the machine learning model is trained on time-series data of a concentration of a biomarker contained in the liquid food item and a near infra-red radiation (NIR) signature for prediction of quality in terms of a remaining shelf life;

perform, a correlation of the plurality of derived features with the concentration of the biomarker contained in the liquid food item, and estimating the remaining shelf-life of the liquid food item based on the concentration of the biomarker, wherein NIR signature of the concentration of the biomarkers contained in the liquid food item is monitored, wherein the NIR signature represents changes in the NIR reflection spectra due to change of chemical composition over time due to degradation of the liquid food items, and wherein a spoilage of the liquid food item contained in the enclosed package is detected by correlating the NIR signature to a biomarker threshold for considering degradation in quality, and to label the liquid food item in terms of a quality index with respect to the biomarker threshold;

estimate, the quality of the liquid food item based on the correlation and the estimated remaining shelf-life; and display to the user on the mobile application, the quality of the liquid food item based on the correlation and the estimated remaining shelf-life.

6. The system of claim 5, wherein the semi-transparent window configured on the enclosed package is used for near infra-red radiation (NIR) imaging.

7. The system of claim 5, wherein step of training the machine learning model further comprises:
(i) obtaining a training dataset comprising of a plurality of training features derived from the near infra-red radiation (NIR) reflection spectra obtained over the range of frequencies and a plurality of concentration of training biomarkers, wherein the near infra-red radiation (NIR) reflection spectra and the concentration of the training biomarkers are associated with a plurality of liquid food items;
(ii) performing a correlation of the plurality of training features derived from the near infra-red radiation (NIR) reflection spectra with the plurality of concentration of the training biomarkers comprised in the obtained training dataset;
(iii) estimating the remaining shelf-life of the plurality of liquid food items based on the plurality of concentration of the training biomarkers; and
(iv) training the machine learning model to estimate the quality of the liquid food item based on the obtained correlation and the estimated remaining shelf-life.

8. The system of claim 5, wherein the biomarker used in the estimation of the quality of the liquid food item is specific to the liquid food item contained inside the enclosed package.

9. One or more non-transitory machine-readable information storage mediums comprising one or more instructions which when executed by one or more hardware processors cause:
transmitting, a near infra-red radiation (NIR) signal over a range of frequencies using a near infra-red radiation (NIR) device through a semi-transparent window configured on an enclosed package containing a liquid food item, wherein the semi-transparent window is configured on a portion of the enclosed package for transmitting the near infra-red radiation (NIR) signal on to the liquid food item;
scanning, by a user via a mobile application, a near infra-red radiation (NIR) reflection spectra resulting from reflection of the near infra-red radiation (NIR) signal over the liquid food item;
transmitting by the user via the mobile application, a data related to the near infra-red radiation (NIR) reflection to an electronic device having a machine learning model;
deriving, using the machine learning model, a plurality of features from the near infra-red radiation (NIR) reflection spectra obtained, wherein the machine learning model runs in a background of the mobile application and the machine learning mode is trained on a near infra-red radiation (NIR) spectra obtained over a range of frequencies to characterize the liquid food item and correlate with quality, wherein the plurality of features comprises an area under a curve of the NIR reflection spectra, localized changes in a slope across the curve, height of peaks of the curve, mean, variance, spread of the curve, wavelengths of the peaks, and wherein the machine learning model is trained on time-series data of a concentration of a biomarker contained in the liquid food item and a near infra-red radiation (NIR) signature for prediction of quality in terms of a remaining shelf life;
performing, a correlation of the plurality of derived features with the concentration of the biomarker contained in the liquid food item, and estimating the remaining shelf-life of the liquid food item based on the concentration of the biomarker, wherein NIR signature of the concentration of the biomarkers contained in the liquid food item is monitored, wherein the NIR signature represents changes in the NIR reflection spectra due to change of chemical composition over time due to degradation of the liquid food items, and wherein a spoilage of the liquid food item contained in the enclosed package is detected by correlating the NIR signature to a biomarker threshold for considering degradation in quality, and to label the liquid food item in terms of a quality index with respect to the biomarker threshold;
estimating, the quality of the liquid food item based on the correlation and the estimated remaining shelf-life; and
displaying to the user on the mobile application, the quality of the liquid food item based on the correlation and the estimated remaining shelf-life.

10. The one or more non-transitory machine readable information storage mediums of claim 9, wherein the semi-transparent window configured on the enclosed package is used for near infra-red radiation (NIR) imaging.

11. The one or more non-transitory machine readable information storage mediums of claim 9, wherein step of training the machine learning model further comprises:
(i) obtaining a training dataset comprising of a plurality of training features derived from the near infra-red radiation (NIR) reflection spectra obtained over the range of frequencies and a plurality of concentration of training biomarkers, wherein the near infra-red radiation (NIR) reflection spectra and the concentration of the training biomarkers are associated with a plurality of liquid food items;

(ii) performing a correlation of the plurality of training features derived from the near infra-red radiation (NIR) reflection spectra with the plurality of concentration of the training biomarkers comprised in the obtained training dataset;

(iii) estimating the remaining shelf-life of the plurality of liquid food items based on the plurality of concentration of the training biomarkers; and (iv) training the machine learning model to estimate the quality of the liquid food item based on the obtained correlation and the estimated remaining shelf-life.

12. The one or more non-transitory machine readable information storage mediums of claim 9, wherein the biomarker used in the estimation of the quality of the liquid food item is specific to the liquid food item contained inside the enclosed package.

* * * * *